United States Patent
Qin

(10) Patent No.: US 11,918,225 B2
(45) Date of Patent: Mar. 5, 2024

(54) LAPAROSCOPIC STAPLER HAVING BIO-GLUE IN SEPARATE POCKET TO AID IN ANASTOMOSIS

(71) Applicant: Cilag GmbH International, Zug (CH)

(72) Inventor: Mingyang Qin, Germany (DE)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/758,253

(22) PCT Filed: Nov. 2, 2018

(86) PCT No.: PCT/CN2018/113756
§ 371 (c)(1),
(2) Date: Apr. 22, 2020

(87) PCT Pub. No.: WO2019/091342
PCT Pub. Date: May 16, 2019

(65) Prior Publication Data
US 2020/0315626 A1    Oct. 8, 2020

(51) Int. Cl.
*A61B 17/115*    (2006.01)
*A61B 17/00*    (2006.01)
*A61B 17/072*    (2006.01)

(52) U.S. Cl.
CPC ...... *A61B 17/115* (2013.01); *A61B 17/00234* (2013.01); *A61B 17/00491* (2013.01); *A61B 2017/07257* (2013.01); *A61B 2017/07264* (2013.01); *A61B 2017/07285* (2013.01)

(58) Field of Classification Search
CPC ........................... A61B 17/115; A61B 17/1155
USPC ...................................................... 227/180.1
See application file for complete search history.

(56) References Cited

U.S. PATENT DOCUMENTS

| 6,193,129 B1 * | 2/2001 | Bittner ................ A61B 17/1114 |
| | | 227/19 |
| 2002/0165559 A1 | 11/2002 | Grant et al. |
| 2006/0085032 A1 * | 4/2006 | Viola ................... A61B 17/115 |
| | | 606/219 |
| 2008/0110958 A1 | 5/2008 | McKenna et al. |
| 2009/0120994 A1 | 5/2009 | Murray et al. |

(Continued)

FOREIGN PATENT DOCUMENTS

| CN | 103917170 A | 7/2014 |
| JP | 2006-110325 A | 4/2006 |
| WO | WO-03094746 A1 * | 11/2003 ....... A61B 17/00491 |

(Continued)

OTHER PUBLICATIONS

Supplementary European Search and Written Opinion dated Jul. 5, 2021 for Application No. 18876233.0, 10 pages.

(Continued)

*Primary Examiner* — Michelle Lopez
(74) *Attorney, Agent, or Firm* — Frost Brown Todd LLP

(57) ABSTRACT

A laparoscopic stapler for stapling tissue is provided for better anastomosis with less leakage. The laparoscopic stapler comprises a staple housing assembly operable to drive staples toward an anvil assembly to perform tissue stapling, wherein the staple housing assembly comprises a pocket for containing bio-glue so that upon tissue stapling, the bio-glue is released and delivered into tissue clamped between the staple housing assembly and the anvil assembly for tissue gluing.

17 Claims, 3 Drawing Sheets

(56) References Cited

U.S. PATENT DOCUMENTS

2010/0127039 A1    5/2010   Hessler
2011/0089219 A1    4/2011   Hessler

FOREIGN PATENT DOCUMENTS

WO    WO 2005/027983 A2    3/2005
WO    WO 2013/019697 A2    2/2013

OTHER PUBLICATIONS

International Search Report and Written Opinion dated Jan. 21, 2019 for Application No. PCT/CN2018/113756, 7 pages.
Japanese Office Action, Notice of Reasons for Refusal, dated Sep. 27, 2022 for Application No. JP2020-525940, 5 pgs.

\* cited by examiner

LAPAROSCOPIC STAPLER HAVING BIO-GLUE IN SEPARATE POCKET TO AID IN ANASTOMOSIS

FIELD OF THE INVENTION

The present invention generally relates to a surgical stapler. More particularly, the present invention relates to a laparoscopic stapler having bio-glue in a separate pocket to aid in anastomosis.

BACKGROUND OF THE INVENTION

In some settings, a surgeon may want to position a surgical instrument through an orifice formed in the body of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions of the tissue may need to be recoupled together. One of such tools for accomplishing these anastomotic procedures is a circular stapler.

Due to the minimum invasive nature of the laparoscopic approach, laparoscopic surgery is deemed the best for some patients. However, existing circular staplers are not a feasible option for modern minimal invasive laparoscopic surgery. In particular, they can only be used in laparoscopic assisted surgery and can't be used in total laparoscopic surgery since they are too big for typical 12 mm trocars required for laparoscopic surgery.

And, surgeons would prefer the possibility of end-to-end anastomosis in laparoscopic procedure because the tissues are healing better than side-to-end or side-to-side anastomosis. However, there is not an end-to-end anastomosis system available for total laparoscopic surgery today. Moreover, unreliable anastomosis leads to bleeding and leakage. Thus, surgeons still need to reinforce the anastomosis with suture after stapling to avoid of leakage.

With the foregoing in mind, it is desirable to provide a new stapler which is adapted for both total laparoscopic surgery and end-to-end anastomosis without the occurrence of leakage.

SUMMARY OF THE INVENTION

It is, therefore, an object of the present invention to provide a laparoscopic stapler for better anastomosis with less leakage and improved tissue heal.

Accordingly, a laparoscopic stapler for stapling tissue is provided. The laparoscopic stapler comprises a staple housing assembly operable to drive staples toward an anvil assembly to perform tissue stapling, wherein the staple housing assembly comprises a pocket for containing bio-glue so that upon tissue stapling, the bio-glue is released and delivered into tissue clamped between the staple housing assembly and the anvil assembly for tissue gluing.

In one embodiment, the staple housing assembly is a separate assembly selectively which can be moved relative to the anvil assembly.

In one embodiment, the staple housing assembly and the anvil assembly are both substantially T shaped assemblies.

In one embodiment, the pocket includes a plurality of pockets, each of which corresponds to one of a plurality of staple pockets disposed in the staple housing assembly.

In one embodiment, the plurality of pockets is arranged in a plurality of long circular shaped rows like the staple pockets.

In one embodiment, the staple housing assembly further comprises a blade for tissue cutting.

In one embodiment, the staple housing assembly comprises a step driver for pushing out the staples, the bio-glue, and the blade in sequence.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

DESCRIPTION OF THE PREFERRED EMBODIMENTS

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. Accordingly, the drawings and descriptions should be regarded as illustrative in nature and not restrictive.

Figure 1:
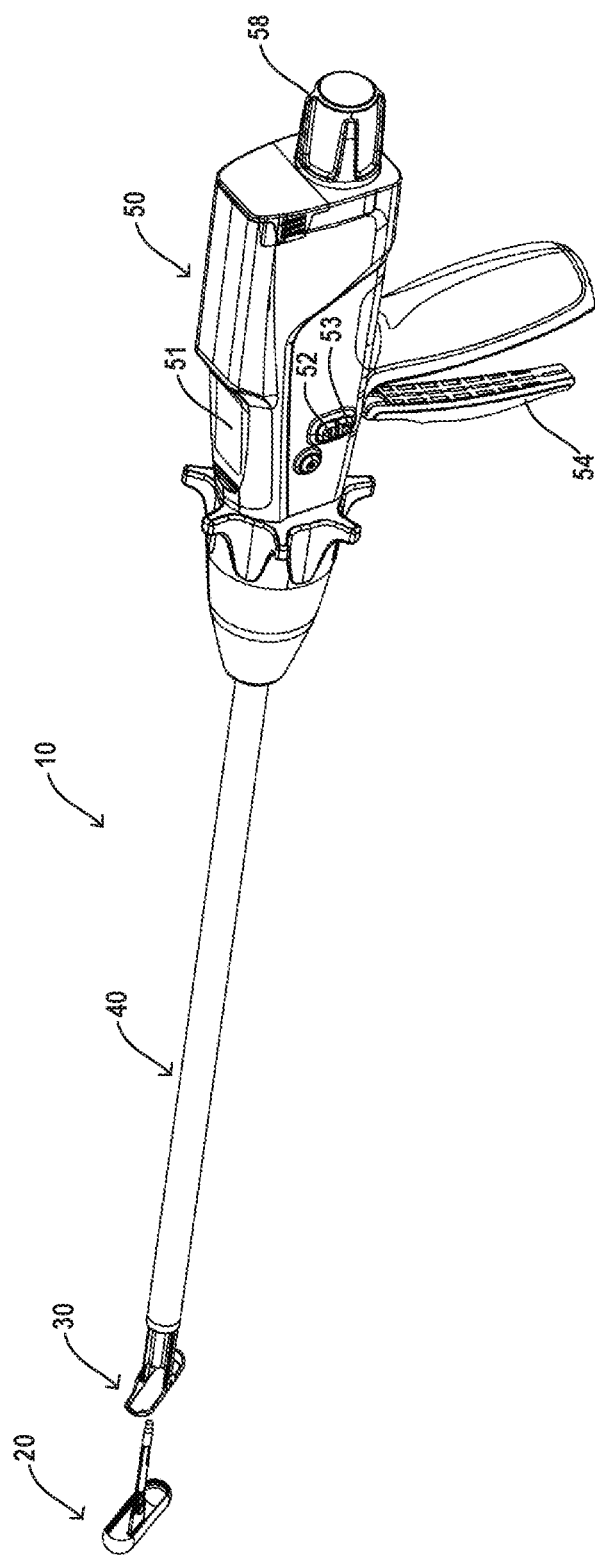
FIG. 1 depicts a perspective view of an exemplary laparoscopic stapler in accordance with the present invention.

FIG. 1 depicts an exemplary laparoscopic stapling instrument 10 having an anvil assembly 30, a shaft assembly 40, and an actuator handle assembly 50. A separate staple housing assembly 20 is configured to be operatively coupleable to a closure system and a trigger system of the instrument. Staple housing assembly 20 is operable to drive staples toward anvil assembly 30 to form the staples when in a coupled position. Shaft assembly 40 extends distally from actuator handle assembly 50, and anvil assembly 30 is coupled to a distal end of shaft assembly 40. In one example, actuator handle assembly 50 is operable to actuate a push trigger of staple housing assembly 20 to drive a plurality of staples out of staple housing assembly 20 that is coupled at the distal end of the instrument. Staples are bent to form completed staples by anvil assembly 30. Accordingly, tissue between the coupled and closed staple housing assembly 20 and anvil assembly 30 may be stapled utilizing instrument 10.

Figure 2:
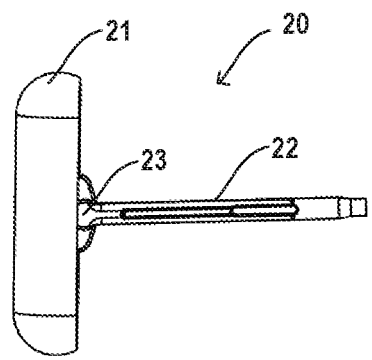
FIG. 2 shows the staple housing assembly used in the laparoscopic stapler of FIG. 1.

As shown in FIG. 2, staple housing assembly 20 is a separate flippable T shaped assembly. In one example, staple housing assembly 20 comprises a staple housing 21 and a housing shaft 22 extending proximally from staple housing 21. Unlike usual circular stapling heads, staple housing 21 according to the present invention has an oblong or long circular shape, such as a shape of rounded rectangle or ellipse. Staple housing 21 is linked to housing shaft 22 via a head pivot 23, for example, and housing shaft 22 is to selectively couple staple housing assembly 20 to the closure system of the instrument. In the embodiment, staple housing assembly 20 is rotatable about a longitudinal axis of the head pivot 23 between a first, linear configuration for delivery and a second, perpendicular configuration as shown for coupling and stapling. It is understood when in the linear configuration, staple housing assembly 20 has a quite low-profile which allows the entire assembly to go through a 12 mm trocar typically used in laparoscopic surgery, and when in the perpendicular configuration, staple housing 21 is pivotal to be perpendicular to housing shaft 22 to exhibit a high-profile. While staple housing assembly 20 is described as selectively coupleable to the closure system in this context, proximal shaft may include a one-way coupling feature such that staple housing assembly 20 cannot be removed from instrument 10 once attached.

Figure 3:
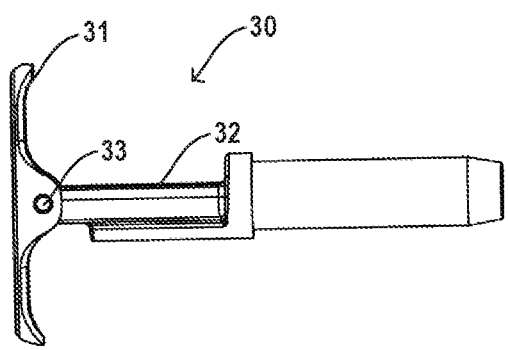
FIG. 3 shows the anvil assembly used in the laparoscopic stapler of FIG. 1.

Anvil assembly 30 of the present example is also flippable to a substantially T shaped and is coupled to a distal end of shaft assembly 40. As shown in FIG. 3, anvil assembly 30 comprises an anvil 31 and an anvil shaft 32 extending proximally from anvil 31. Anvil 31 has a central opening and a long circular staple forming surface at a distal end. Housing shaft 22 of staple housing assembly 20 may go through the opening to be coupled to the closure system of the instrument. Anvil 31 may be also linked to anvil shaft 32 via a head pivot 33, for example. Like staple housing assembly 20, anvil assembly 30 is also configured to be rotatable about a longitudinal axis of head pivot 33 between a first, linear configuration and a second, perpendicular configuration. Also, when in the linear configuration, anvil assembly 30 has a quite low-profile which allows the entire assembly to go through a 12 mm trocar, and when in the perpendicular configuration, anvil 31 pivots to be perpendicular to anvil shaft 32 to present a high-profile of T shape.

Since staple housing assembly 20 is a separate coupleable component, staple housing assembly 20 may be inserted to a portion of tissue in the linear configuration prior to being coupled to the instrument. By way of example only, staple housing assembly 20 may be inserted into a first tubular portion of tissue, such as esophagus, while instrument 10 is inserted into a second tubular portion of tissue, such as jujune. And, since staple housing assembly 20 and anvil assembly 30 can both go through 12 mm trocar in its linear configuration, the stapler according to the present invention can be used in total laparoscopic surgery and thus can be called a laparoscopic stapler. Moreover, the high-profile provided by the T shaped staple housing assembly and anvil assembly allows the stapler according to the present invention to be adapted for a relatively larger lumen to be joined, for example, a lumen with a diameter of 26 mm, 28 mm, 30 mm, 34 mm, 36 mm, 38 mm, 40 mm, or 42 mm.

As stated above, staple housing assembly 20 is operatively coupleable to the closure system and firing system of instrument 10 to staple material clamped between staple housing assembly 20 and anvil assembly 30. After staple housing assembly 20 is coupled, the closure system is operable to longitudinally translate staple housing assembly 20 relative to anvil assembly 30 to clamp tissue therebetween. Once appropriate, the firing system comprising a trigger 54 may be actuated by a user to drive and fire staples from staple housing assembly.

Figure 4:
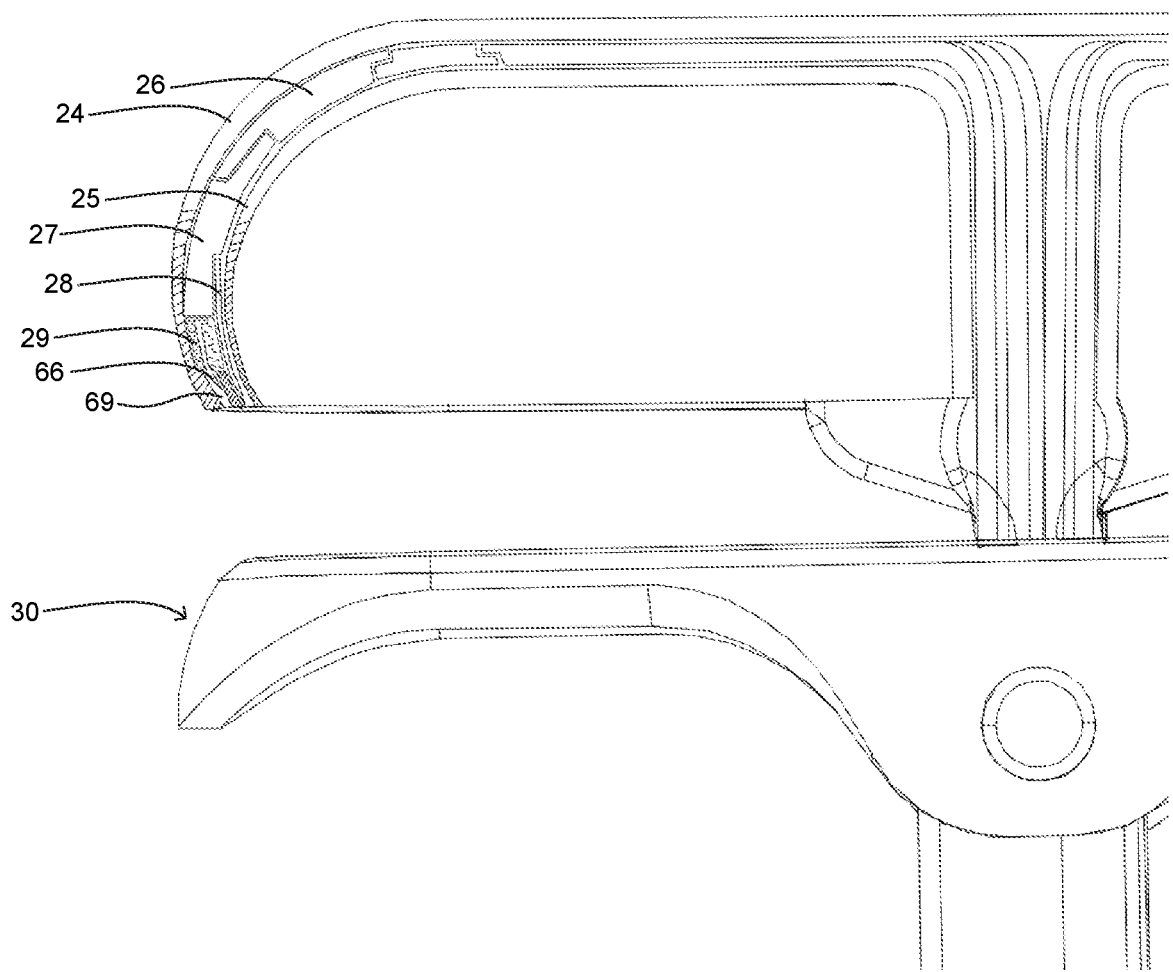
FIG. 4 is a sectional view of the staple housing assembly in accordance with the present invention.

As shown in FIG. 4, staple housing 21 of the present example comprises an outer casing 24 and an inner casing 25. A push trigger 26 is disposed in staple housing 21 and configured to be driven proximally in response to the actuation of trigger 54, which in turn may drive a step driver 27 proximally. Staple housing 21 further includes a blade 28 configured to sever tissue when step driver 27 is actuated proximally. A plurality of staples 66 contained within staple pockets 69 are positioned proximal to step driver 27 such that the proximal actuation of step driver 27 also drives staples 66 proximally.

According to the present invention, staple housing 21 further comprises a plurality of glue pockets 29 for containing bio-glue. Glue pockets 29 are provided so that as step driver 27 drives staples 66 to staple tissue, bio-glue can also be pushed out of staple housing 21 into tissue by the same driver 27. As can be seen from FIG. 4, glue pockets 29 and staple pockets 69 are disposed in a pair of concentric long circular rows. Blade 28 is arranged distal relative to bio-glue and staples 66. As such, when step driver 27 is actuated proximally, it first pushes staples 66 and bio glue out of the respective pocket 69, 29 into tissue for stapling and gluing. Such delivery of bio-glue into tissue may prevent leakage and facilitate tissue heal, and thus providing an improved anastomosis. As step driver 27 is further actuated proximally, it drives blade 28 out to achieve tissue cutting.

The operation of the laparoscopic stapler according to the present invention is now described with respect to an exemplary jujune and esophagus anastomosis.

In this laparoscopic approach, anastomosis is made with a delivery channel provided by 12 mm trocar and in the prepared condition, and ends of jujune and esophagus are closed with for example a linear stapler. In a first step, an opening is made at the prepared closed end of esophagus which may be stabilized with a grasper. A staple housing assembly, such as staple housing assembly 20 described above is inserted through the made opening in its linear configuration and then the assembly 20 is activated to its T shaped configuration to let the housing shaft protrude out of the esophagus end from the opening such that staple housing assembly 20 is ready for coupling. Optionally, the assembly 20 may be stabilized with a grasper, for example. In the next step, inserting the instrument 10 through a 12 mm trocar surgery device and a prepared opening in jujune with anvil assembly 30 in its linear configuration, and then activating the instrument to its T shaped configuration. Jujune wall is now made to a long circular shaped by the T shaped anvil. In a next step, staple housing assembly 20 is coupled to the closure system of instrument and staple housing assembly 20 is actuated proximally towards anvil assembly 30 to close the gap distance therebetween. Once instrument 10 is within operating range, the user actuates trigger 54 of instrument 10 to drive step driver 27 proximally. The actuation of step driver 27 pushes staples and bio-glue into tissue for stapling and gluing and also blade to cut overlapping tissue of esophagus and jujune. With such end-to-end anastomosis having done, the surgeon may return staple housing assembly 20 and anvil assembly 30 back into their linear configuration, and then the stapler may be removed from the patient through the 12 mm trocar.

Many modifications may be made to the described example. It is envisaged when staple housing assembly 20 is coupled to the closure system, the gap distance between a proximal face of staple housing assembly 20 and a distal face of anvil assembly 30 can be reduced. In this regard, the closure system may be translatable longitudinally relative to anvil assembly 30 via an adjusting knob 58 located at a proximal end of actuator handle assembly 50. Accordingly, when staple housing assembly 20 is coupled to the closure system, rotation of adjusting knob 54 reduces gap distance by actuating staple housing assembly 20 relative to anvil assembly 30. For instance, staple housing assembly 20 is actuated proximally relative to anvil assembly 30 from an initial, open position to a closed position, thereby reducing the gap distance and the distance between the two portions of tissue to be joined. Once the gap distance is brought within a predetermined range, staple housing assembly 20 may be fired by a user pivoting trigger 54 of actuator handle assembly 50.

As noted above, gap distance corresponds to the distance between staple housing assembly 20 and anvil assembly 30. When a stapler is inserted into a patient, this gap distance may not be easily viewable. Accordingly, a moveable indicator bar may be provided to be visible through an indicator window positioned on top of actuator handle assembly 50. For example, an indicator bar may be operable to move in response to rotation of adjusting knob 58 such that the position of indicator bar is representative of the gap distance. Moreover, indicator window 51 may further comprise a scale which indicates that the gap is within a desired operating range and a corresponding staple compression representation at each end of scale. Accordingly, a user can view the position of the coupled staple housing assembly 20 relative to the anvil assembly 30 via the indicator bar and the scale.

In a further embodiment according to the present invention, anvil control buttons 52, 53 corresponding to the activation of anvil assembly 30 to its T shaped configuration and to the deactivation of anvil assembly 30 to its original, linear configuration are provided on actuator handle assembly 50, as shown in FIG. 1. With this arrangement, the user may easily return the stapler back to the low profile for removal through the trocar channel.

While the preferred embodiments have been shown and described, it will be understood that there is no intent to limit the invention by such disclosure, but rather, it is intended to cover all modifications and alternate constructions falling within the spirit and scope of the invention.

What is claimed is:

1. A laparoscopic stapler for stapling tissue, comprising:
   (a) a plurality of staples;
   (b) a bio-glue; and
   (c) a staple housing assembly operable to drive the plurality of staples toward an anvil assembly to perform tissue stapling, wherein the staple housing assembly comprises a pocket for containing the bio-glue so that upon tissue stapling, the bio-glue is released and delivered into tissue clamped between the staple housing assembly and the anvil assembly for tissue gluing, wherein the staple housing assembly further comprises a blade for tissue cutting, wherein the staple housing assembly comprises a step driver for pushing out the plurality of staples, the bio-glue, and the blade in sequence, wherein each staple of the plurality of staples is spaced apart from the bio-glue, wherein the staple housing assembly is a separate assembly which can be moved relative to the anvil assembly, wherein the staple housing assembly and the anvil assembly are both substantially T shaped assemblies.

2. The laparoscopic stapler according to claim 1, wherein the pocket includes at least one pocket, each of which corresponds to one of at least one staple pocket disposed in the staple housing assembly.

3. The laparoscopic stapler according to claim 2, wherein the at least one pocket is arranged in at least one long circular shaped rows like the at least one staple pocket.

4. A surgical stapling instrument, comprising:
   (a) an anvil assembly defining at least one staple forming surface; and
   (b) a staple housing assembly configured to drive a plurality of staples against the at least one staple forming surface of the anvil assembly, wherein the staple housing assembly comprises:
      (i) at least one staple pocket, wherein each staple pocket of the at least one staple pocket is configured to receive a corresponding staple of the plurality of staples, and
      (ii) at least one glue pocket, wherein each glue pocket of the at least one glue pocket is configured to receive an adhesive, wherein each glue pocket of the at least one glue pocket is adjacent to and separate from a corresponding staple pocket of the at least one staple pocket;
   (c) the plurality of staples, wherein each staple of the plurality of staples is received within a corresponding staple pocket of the at least one staple pocket; and
   (d) the adhesive, wherein a portion of the adhesive is received within each glue pocket of the at least one glue pocket, wherein each staple of the plurality of staples is spaced apart from the adhesive,
   wherein the staple housing assembly defines a longitudinal axis, wherein each glue pocket of the at least one glue pocket is positioned radially outwardly from the corresponding staple pocket of the at least one staple pocket relative to the longitudinal axis.

5. The surgical stapling instrument of claim 4, wherein each glue pocket of the at least one glue pocket is spaced apart from the corresponding staple pocket of the at least one staple pocket.

6. The surgical stapling instrument of claim 4, wherein each glue pocket of the at least one glue pocket is separated from the corresponding staple pocket of the at least one staple pocket by a corresponding partition.

7. The surgical stapling instrument of claim 4, wherein each staple pocket of the at least one staple pocket is disposed in a first row, wherein each glue pocket of the at least one glue pocket is disposed in a second row different from the first row.

8. The surgical stapling instrument of claim 7, wherein the first and second rows are concentric.

9. The surgical stapling instrument of claim 4, further comprising a driver and a blade, wherein the driver is configured to, in a predetermined sequence, deploy the adhesive from each glue pocket of the at least one glue pocket for gluing tissue, deploy each staple from the corresponding staple pocket of the at least one staple pocket for stapling the tissue, and drive the blade for severing the tissue.

10. The surgical stapling instrument of claim 9, wherein the driver is configured to initially deploy the adhesive from each glue pocket of the at least one glue pocket for gluing tissue and deploy each staple from the corresponding staple pocket of the at least one staple pocket for gluing and stapling the tissue, and to subsequently drive the blade for severing the tissue.

11. The surgical stapling instrument of claim 9, wherein the driver includes a step driver.

12. A surgical stapling instrument, comprising:
   (a) an anvil assembly defining at least one staple forming surface; and
   (b) a staple housing assembly configured to drive a plurality of staples against the at least one staple forming surface of the anvil assembly, wherein the staple housing assembly comprises:
      (i) at least one staple pocket, wherein each staple pocket of the at least one staple pocket is configured to receive a corresponding staple of the plurality of staples, (ii) at least one glue pocket, wherein each glue pocket of the at least one glue pocket is configured to receive an adhesive, (iii) a blade, wherein the blade is configured to sever tissue, and (iv) a step driver, wherein the step driver includes at least one proximal surface for deploying the adhesive and the plurality of staples, wherein the step driver includes a distal ledge for driving the blade, wherein the distal ledge is distal of the at least one proximal surface.

13. The surgical stapling instrument of claim 12, wherein the step driver is configured to, in a predetermined sequence:

(A) deploy the adhesive from each glue pocket of the at least one glue pocket via the at least one proximal surface for gluing tissue, (B) deploy each staple from the corresponding staple pocket of the at least one staple pocket via the at least one proximal surface for stapling the tissue, and (C) drive the blade via the distal ledge for severing the tissue.

14. The surgical stapling instrument of claim 13, wherein the step driver is configured to drive the blade for severing the tissue after deploying the adhesive from each glue pocket of the at least one glue pocket and deploying each staple from the corresponding staple pocket of the at least one staple pocket.

15. The surgical stapling instrument of claim 12, further comprising:

(a) the plurality of staples, wherein each staple of the plurality of staples is received within a corresponding staple pocket of the at least one staple pocket; and (b) the adhesive, wherein a portion of the adhesive is received within each glue pocket of the at least one glue pocket.

16. The surgical stapling instrument of claim 15, wherein each staple of the plurality of staples is spaced apart from the adhesive.

17. The surgical stapling instrument of claim 12, wherein each glue pocket of the at least one glue pocket is separated from a corresponding staple pocket of the at least one staple pocket by a corresponding partition.

* * * * *